US007771970B2

(12) United States Patent
Lee et al.

(10) Patent No.: US 7,771,970 B2
(45) Date of Patent: Aug. 10, 2010

(54) PROCESS FOR PREPARATION OF POLYPEPTIDES OF INTEREST FROM FUSION POLYPEPTIDES

(75) Inventors: Woo-Jong Lee, Daejeon (KR); Heung-Bok Park, Daejeon (KR); Tae-Hoon Cho, Suwon (KR); Jeong-Min Kim, Gyeongsangbuk-do (KR); Yeon-Sung Park, Goyang (KR)

(73) Assignee: Advanced Protein Technologies Corporation (KR)

( * ) Notice: Subject to any disclaimer, the term of this patent is extended or adjusted under 35 U.S.C. 154(b) by 112 days.

(21) Appl. No.: 10/484,478

(22) PCT Filed: Jul. 26, 2002

(86) PCT No.: PCT/KR02/01416

§ 371 (c)(1),
(2), (4) Date: Feb. 9, 2005

(87) PCT Pub. No.: WO03/010204

PCT Pub. Date: Feb. 6, 2003

(65) Prior Publication Data

US 2005/0124790 A1    Jun. 9, 2005

(30) Foreign Application Priority Data

Jul. 26, 2001   (KR)   ................. 2001-45229
Jul. 25, 2002   (KR)   ................. 2002-43968

(51) Int. Cl.
C12P 21/00       (2006.01)
(52) U.S. Cl. ........................... 435/69.7; 530/416
(58) Field of Classification Search .............. 435/69.7
See application file for complete search history.

(56) References Cited

U.S. PATENT DOCUMENTS

| 4,431,739 | A |   | 2/1984 | Riggs |
| 4,532,207 | A |   | 7/1985 | Brewer et al. |
| 4,743,679 | A |   | 5/1988 | Cohen et al. |
| 4,987,070 | A |   | 1/1991 | Magota et al. |
| 5,108,919 | A |   | 4/1992 | Liu et al. |
| 5,179,196 | A |   | 1/1993 | Johnson et al. |
| 5,196,321 | A |   | 3/1993 | Bachmair et al. |
| 5,322,930 | A |   | 6/1994 | Tarnowski et al. |
| 5,620,923 | A | * | 4/1997 | Rechsteiner et al. ....... 435/69.7 |
| 5,914,254 | A |   | 6/1999 | Mascarenhas et al. |
| 6,068,994 | A |   | 5/2000 | Barr |

FOREIGN PATENT DOCUMENTS

| WO | WO 92/02550 | 2/1992 |
| WO | WO 9423040 | 10/1994 |
| WO | WO 00/03011 | 1/2000 |
| WO | WO 0200892 | 1/2002 |
| WO | WO 02/057462 | 7/2002 |

OTHER PUBLICATIONS

Baker et al. Protein Expression Using Cotranslational Fusion and Cleavage of Ubiquitin. The Journal of Biological Chemistry. 1994. vol. 269, No. 41, pp. 25381-25386.*
Amersham Biosciences GST Fusion System Handbook, 1997, www4.amershambiosciences.com/aptix/upp01077.nsf/Content/orderonline_handbooks.*
Amersham Biosciences Ion Exchange Chormatography and Chromatofocusing Handbook, 1997, www4.amershambiosciences.com/aptix/upp01077.nsf/Content/orderonline_handbooks.*
Larsen et al., Substrate Binding and Catalysis by Ubiquitin C-terminal Hydrolases: Identification of Two Active site Residues. Biochemistry, 1996, vol. 35, pp. 6735-6744.*
Baker et al. Protein Expression Using Ubiquitin Fusion and Cleavage. Current Opinion in Biotechnology, 1996, vol. 7, pp. 541-546.*
Cudney R. Protein Crystallization and Dumb Luck. The Rigaku Journal. 1999. vol. 16, No. 1, pp. 1-7.*
Drenth, "Principles of Protein X-Ray Crystallography", 2nd Edition, 1999 Springer-Verlag New York Inc., Chapter 1, p. 1-21.*
Kundrot, C.E. Which Strategy for a Protein Crystallization Project? Cellular Molecular Life Science. 2004. vol. 61, pp. 525-536.*
McPherson, A. Current Approaches to Macromolecular Crystallization. European Journal of Biochemistry. 1990. vol. 189, pp. 1-23.*
Blanke Steven R., et al, (1996) "Fused polycationic peptide mediates delivery of diphtheria toxin A chain to the cytosol in the presence of anthrax protective antigen" Proceedings of the National Academy of Sciences. vol. 936, No. 16:84370-8442.
Butt, T.R., et al (1988) "Ubiquitin-Metallothionein Fusion Protein Expression in Yeast" Journal of Biological Chemistry 263 (31) 16364-16371.
Kohno, T , et al, (1998) "A new general method for the biosynthesis of stable isotope-enriched pptides using a decahistidine-tagged ubiquitin fusion system" Journal of Biomolecular NMR., vol. 12, No. 1.

(Continued)

Primary Examiner—Suzanne M. Noakes
(74) Attorney, Agent, or Firm—Pearl Cohen Zedek Latzer, LLP; Mark S. Cohen

(57) ABSTRACT

The present invention relates to a process of separation a protein of interest comprising expressing the protein of interest fused with a fusion partner, selectively adsorbing on matrix, and performing efficient cleavage reaction on the fusion protein adsorbed on matrix or separated from the matrix, and recovering the protein of interest. Also, the present invention provides a fusion protein comprising a protein of interest and a fusion partner, wherein the fusion partner comprises an amino acid sequence which can be cleaved by ubiquitin cleavage enzyme at its C-terminus, and which has a difference in isoelectric point of 1 or more from the protein of interest. According to the present invention, the proteins of interest can be purified in high yield and purity. In addition, complicated separating processes required in the production of recombinant proteins can be eliminated so as to cut down the production cost.

4 Claims, 9 Drawing Sheets

OTHER PUBLICATIONS

Kweon, D., et al (2002) "Characterazation of polycationic amino acids fusion systems for ion-exchange purifucation of cyclodextrin glycosyltransferase from recombinant *Escherichia coli*" Biotechnology Progress, vol. 18, No. 2:303-308.

Stempfer, G., et al (1996) "Improved refolding of an immobilized fusion protein" Bio/Technology, Nature vol. 14, No. 3.

* cited by examiner

PROCESS FOR PREPARATION OF POLYPEPTIDES OF INTEREST FROM FUSION POLYPEPTIDES

CROSS-REFERENCE TO RELATED APPLICATIONS

This application is a National Phase Application of PCT International Application No. PCT/KR02/01416, International Filing Date 26 Jul. 2002, claiming priority of Korean Patent Applications 2001-45229, filed 26 Jul. 2001, and 2002-43968, filed 25 Jul. 2002.

BACKGROUND OF THE INVENTION (a) Field of the Invention

The present invention relates to a process for separating the protein of interest from fusion protein which comprises a protein of interest and a fusion partner, and a fusion protein useful for the process.

(b) Description of the Related Art

As the genetic recombinant technology develops, the proteins which are difficult to obtain from nature can be produced in a large quantity by using fermentation of genetically engineered organism, thereby contributing to the human welfare. Hosts used for the recombinant technologies include E. coli, yeast, animal cell, etc. Especially, E. coli has the advantages for protein production in that the gene can be easily manipulated, gives high yield production, and allows use of inexpensive medium.

When a protein of interest is produced by using the recombinant E. coli, the protein can be expressed in soluble form or insoluble inclusion body, depending on their properties. The protein expressed in soluble form has its natural property due to accurate protein folding. The proteins that can coagulate together to be insoluble before forming tertiary structure do not show their natural properties. Thus, the inclusion body of insoluble protein must be solubilized according to various methods and then be refolded. In latter case, the yield and production rate of refolding process are low. Furthermore, many disulfide bonds in the insoluble protein make accurate refolding difficult. Therefore, it is advantageous to produce the protein of interest in soluble form.

When the protein of interest is expressed in soluble form, it is possible to largely reduce the number of early separation steps such as centrifugation and filtration by using expanded bed adsorption (EBA) to substantially increase the yield and productivity of the protein. To express the protein of interest in soluble form, a fusion partner which is capable to be well expressed in soluble form can be fused together with the protein of interest. The examples of fusion partner include GST, maltose binding protein, thioredoxin, ubiquitin, etc. The ubiquitin is a small peptide consisting of 76 amino acids. When the protein of interest is expressed in a fusion peptide with ubiquitin, the ubiquitin cause the protein to be well expressed in soluble form as well as to increase the expression rate, thereby making the protein in active form.

On the other hand, it is difficult to recover pure protein when the protein of interest is expressed in soluble form. When the protein of interest is expressed in insoluble inclusion body, it is easy to separate the inclusion body from soluble materials derived from E. coli such as the proteins of host cell, DNA, polysaccharides in the early stage of purification. However, it is very difficult to separate soluble protein of interest because it is mixed with the soluble contaminants such as the proteins of host cell, DNA, polysaccharides. The inclusion body can be solubilized by adding detergents such as urea before disrupting cells in order to purify the inclusion body with EBA, which loses advantage of separating insoluble inclusion body from soluble materials derived from E. coli as described above. In conclusion, when the protein of interest is expressed in a soluble form, or to be applied by EBA process, the protein of interest mixed with DNA, and polysaccharides enters subsequent purification steps. Thus, the efficient purification process is still required.

In typical purification processes, the protein of interest can be recovered from intracellular proteins by using the difference in charge, solubility, size, hydrophobicity, etc. These purification processes employ inexpensive materials, but have a low selectivity. Thus, to obtain the desired purity, many purification steps comprising various methods are required, and the purification yield decreases largely through the purification steps. In addition, these methods have a problem wherein the purification steps must be optimized to satisfy the property of the each individual protein of interest. To increase the selectivity of the protein of interest, the affinity chromatography can be commonly used where an antibody recognizing the unique structure of the protein is immobilized on resin, or a tag with affinity to specific support can be used as a fusion partner. The examples used for increasing selectivity include GST, polyhistidine, etc. (U.S. Pat. No. 5,108,919, and Korean Patent No. 177304). In case of affinity chromatography, expensive resin having affinity to the fusion partner or protein of interest restricts industrial application.

In addition, when the protein of interest is expressed in fusion protein, the fusion partner must be removed by cleavage in the subsequent step. In particular, when the protein of interest is intended for medical use, the fusion peptide must be designed to have the suitable cleavage site between the protein of interest and a fusion partner to produce an accurate N-terminus or C-terminus after cleavage, and not to have the cleavage site inside of the protein of interest. The cleavage reaction can be performed with chemical reagents such as acid and CNBr, and proteases such as Factor Xa, and enterokinase. Even though the enzymes have a relatively high selectivity, it is still possible to cleave the other site than intended cleavage site; furthermore, it has a poor efficiency and high cost.

Prior to the present invention, it was developed that a fusion peptide contained a fusion partner which was different in isoelectric point from the protein of interest, and was prepared and separated with ion exchange chromatography. U.S. Pat. No. 4,532,207 disclosed that the Arginine tag was fused with anionic EGF, and then purified through cation exchange chromatography to produce EGF. However, the method has a disadvantage in that the charge of a few ionic amino acids directly attached to C-terminus of protein of interest is masked by opposite charge of large protein of interest and so fusion protein cannot adsorb on the matrix efficiently. Thus the method has a low yield of purification.

In U.S. Pat. Nos. 5,179,196 and 5,322,930, the fusion peptides consisting of a fusion partner which is different from the protein of interest in the electric property, the protein of interest and CNBR cleavage site and Staph V8 cleavage site, respectively. However, the patents have a problem in that many proteins having a similar isoelectric point as well as the fusion protein can also adsorb on ion exchange chromatograph, and the cleavage method has a poor selectivity. Thus, the other proteins adsorbed on chromatograph are cleaved and solubilized together with the protein of interest.

SUMMARY OF THE INVENTION

The present invention provides a DNA construct to separate a protein of interest in high yield conveniently.

The present invention also provides a fusion protein comprising a protein of interest and a fusion partner to separate a protein of interest in high yield conveniently and efficiently.

The present invention also provides a process for separating a protein of interest in high yield conveniently and efficiently.

The present invention provides a process for separating a protein of interest by using the change of isoelectric point.

DETAILED DESCRIPTION OF THE PREFERRED EMBODIMENT

Figure 1:
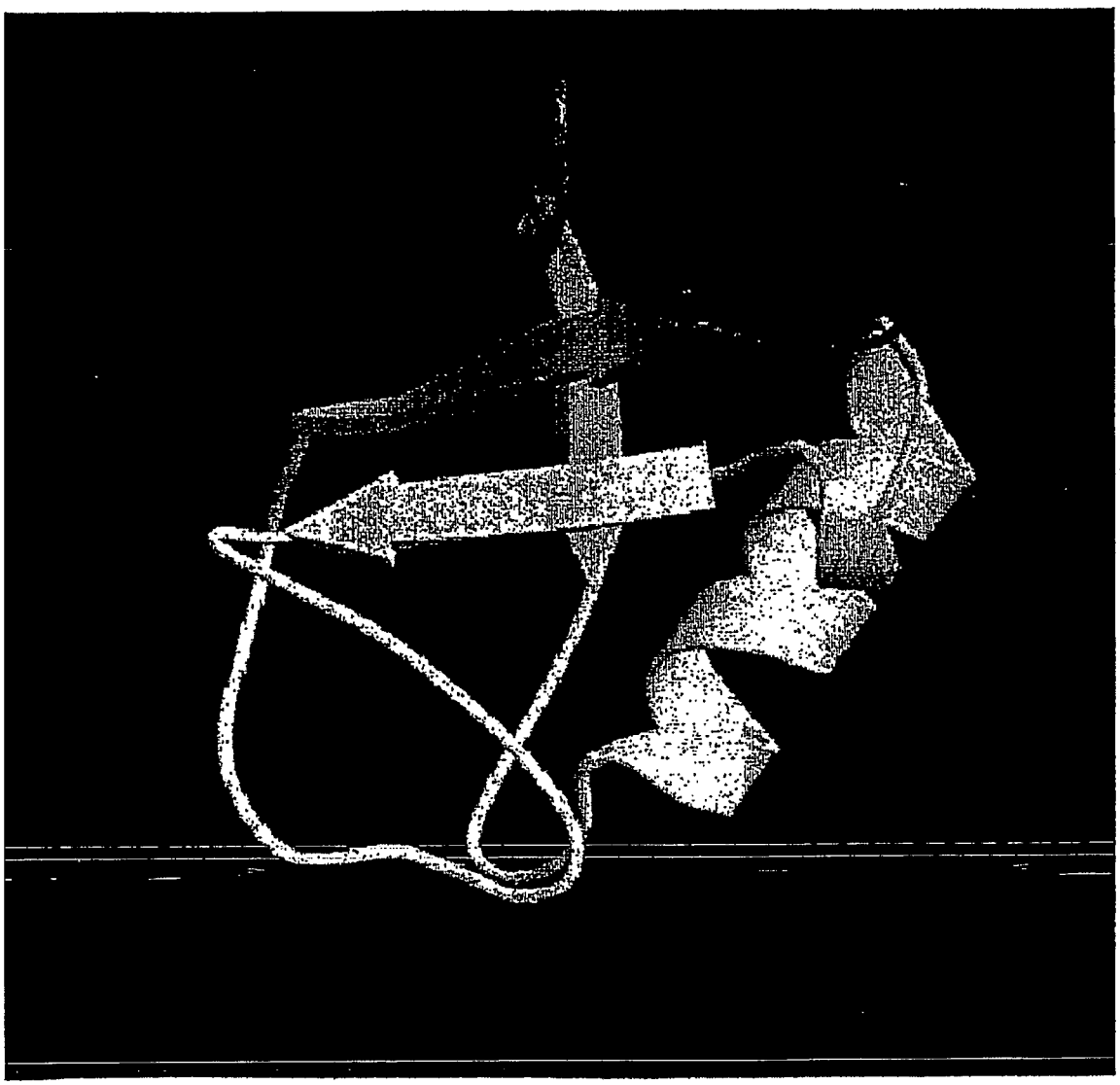
FIG. 1 shows a schematic tertiary structure of ubiquitin.

The present invention relates to a process for separating the protein of interest from fusion protein comprising a protein of interest and a fusion partner, and a fusion protein useful for the process.

More specifically, the present invention provides a fusion protein comprising a protein of interest and a fusion partner, wherein the fusion partner comprises an amino acid sequence to be cleaved with ubiquitin cleavage enzyme on its C-terminus, and wherein the difference of isoelectric point between the protein of interest and the fusion partner is at least 1.

Unless specifically mentioned otherwise, the terms, "protein," "peptide," and "polypeptide" are used interchangeably.

The term, "ubiquitin cleavage enzyme" is intended to mean an enzyme that cleaves a peptide bond next to RGG at C-terminus of protein such as ubiquitin in eukaryotic cell. For example, the enzymes include UBP1 and UBP2 derived from *Saccharomyces cerevisiae*, UBP41 in muscle cell, etc. As the ubiquitin cleavage enzyme accurately cleaves a peptide bond next to Glycine which is the 76$^{th}$ amino acid of ubiquitin, it is possible to generate an accurate N-terminal residue in protein of interest (U.S. Pat. No. 5,847,097).

In the present invention, ubiquitin can be modified to include a tag which comprises 6-10 amino acids selected from a group consisting of His, Lys, and Arg. For examples, the modified ubiquitin can be polyhistidine, polylysine, or polyarginine, etc.

The term "protein of interest" is intended to mean a protein to be prepared, and includes physiologically active proteins such as growth hormone, interferon, interleukin, granulocyte colony stimulating factor, erythropoietin, and insulin.

Herein, the term "fusion partner" is intended to mean a peptide which comprises an amino acid sequence, for example RGG, which can be cleaved by ubiquitin cleavage enzyme in its C-terminus, and which has an isoelectric point difference of 1 or more, preferably 1.5 or more, more preferably 2 or more than that of the protein of interest. The preferred fusion partner is a peptide to make the protein of interest express in soluble form. That is, the fusion partner may include peptides i) the ubiquitin cleavage site that amino acid sequence can be cleaved by ubiquitin cleavage enzyme at C-terminus such as ubiquitin, a part, and a peptide derived therefrom and, and ii) a peptide or variants thereof to make the fusion protein express in soluble from such as glutathione S transferase (GST), maltose binding protein, or thioredoxin at N-terminus of the ubiquitin cleavage site.

In an embodiment of the present invention, at least an amino acid in the fusion partner can be substituted, deleted, or inserted to make the difference of isoelectric point at least 1.

The fusion partner can include a peptide where the charge can be changed by including amino acid sequence which has a different charge from that of the protein of interest at N-terminal or internal site of the fusion partner. The amino acid sequence which has a different charge from that of the protein of interest can be amino acid sequence consisting of at least a kind of amino acid selected from His, Lys and Arg. Preferably, The amino acid sequence can be a peptide consisting of 2-30 amino acids, for examples polyhistidine, polylysine, and polyarginine.

Alternatively, the amino acid sequence which has a different charge from that of the protein of interest can be an amino acid sequence consisting of at least a kind of amino acid selected from glutamic acid and aspartic acid. Preferably, the amino acid sequence can be a peptide consisting of 2-30 amino acids, for examples polyglutamate, polyaspartate, etc. For examples, the fusion partners can include ubiquitin, parts or variants thereof, and a synthetic peptide comprising ubiquitin or ubiquitin cleavage site, which include amino acid sequence having a different charge from that of the protein of interest at its N-terminus or internal site.

Herein, the term "amino acid sequence having a different charge from that of the protein of interest" means an amino acid sequence which has a different charge from that of the protein of interest under the pH condition used in the purification process of the fusion protein or the protein of interest, thereby causing the adsorption difference on matrix between protein of interest and the fusion partner. If pH of the protein of interest is known, it is possible to design an amino acid sequence to make the charge difference. For examples, when the protein of interest has isoelectric point of 7 or less, amino acid sequence linked continuously at least two positively-charged amino acids such as Lys and Arg can be used. When the protein of interest has isoelectric point of 7 or more, amino acid sequence linked continuously at least two negatively-charged amino acids such as Glutamic acid and Aspartic acid can be used.

The amino acid sequence having a different charge from that of the protein of interest can be located at N-terminal or internal site of the fusion partner. It is possible to easily change the adsorption degree of the fusion partner and the protein of interest on matrix, for examples ion exchange resin or membrane by changing the charge of the fusion partner.

While most of proteins for medical use have isoelectric point of 7.0 or less, nucleic acids and endotoxin in cell extract also show a low isoelectric point distribution. Thus, it is possible to separate the fusion protein from contaminants derived from cell by combining the protein of interest with the fusion partner of high pI.

For example, because the ubiquitin has pI of 6.56 which is close to a neutral pI value, it is difficult to separate the weak acidic protein of interest from the contaminating materials such as nucleic acids, endotoxin and proteins of host cell by using ion exchange resin or membrane based on the isoelectric point difference. In such case, it is possible to increase pI of the fusion protein by modifying ubiquitin with cationic peptide tag inserted into the N-terminal or internal site of ubiquitin to produce the fusion protein comprising the modified ubiquitin and the protein of interest. Thus, the fusion protein can be easily separated from the contaminating materials derived from the host cell.

In addition, tag including ionic amino acids can be ligated to N-terminus of ubiquitin to induce the isoelectric point difference between the protein of interest and the fusion partner to be cleaved by ubiquitin cleavage enzyme. Furthermore, the ubiquitin can be modified by substituting at least an amino acid of ubiquitin, or by inserting an ionic amino acid therein.

The fusion partner of the present invention can be a modified ubiquitin where at least an amino acid located on surface of tertiary structure of ubiquitin can be substituted to have a different charge. For example, at least an amino acid located on surface of tertiary structure of ubiquitin can be substituted with at least an amino acid selected from His, Lys, and Arg, or with at least an amino acid selected from Glu and Asp.

In reference to the tertiary structure of ubiquitin as shown FIG. 1 (Vijay-Kumar et al., J Mol Biol 194: pp. 531 (1987)), amino acids suitable for being substituted can be selected. The amino acid which can be substituted in the fusion partner satisfies the requirements that the substitution of the amino acid changes the surface charge of ubiquitin without changing the tertiary structure of ubiquitin in order to make the ubiquitin cleavage enzyme recognize the fusion protein after the substitution. The amino acid to be substituted can be selected from amino acids which are located on loop but not within secondary structure of alpha-helix and beta-sheet in secondary structure, and which are located on surface of tertiary structure.

The fusion partner can be selected from modified ubiquitin where the amino acids on at least a site selected from a group of consisting Glu 16, Glu 18, and Glu 64 can be substituted. Preferably, amino acids on Glu 16, Glu 18, and Glu 64 can be substituted with Arg, Lys, and Arg, respectively.

In the present invention, the term "cell extract" is intended to include cell lysate, and culture solution which contains the fusion protein comprising the protein of interest.

The present invention provides a process for separating the protein of interest by using the fusion protein.

In addition, the present invention provides a process for separating a protein of interest from a fusion protein comprising:

a) expressing a fusion protein comprising the protein of interest and the fusion partner in a host cell;

b) loading the fusion protein on matrix where the fusion partner can adsorb;

c) treating the adsorbed matrix with ubiquitin cleavage enzyme; and d) eluting the cleaved protein of interest from the matrix.

The present invention also provides a process of separating a protein of interest from a fusion protein comprising:

a) expressing a fusion protein comprising the protein of interest and the fusion partner in the host cell;

b) loading the fusion protein on matrix where the fusion partner can adsorb;

c) recovering the fusion protein from the matrix;

d) treating the recovered fusion protein with ubiquitin cleavage enzyme; and e) separating the protein of interest from the fusion partner by using the adsorption difference on matrix between the protein of interest and the fusion partner.

Among the above steps of separating the protein of interest, the step loading the fusion partner on matrix in step b) can be performed by i) loading the cell extract including the fusion protein on matrix which the fusion partner can adsorb, or ii) by loading the cell extract including the fusion protein on matrix which the protein of interest can adsorb, recovering the fusion protein from the matrix, and loading the recovered fusion protein on matrix which the fusion partner can adsorb.

The matrix can be an ion exchange resin or a membrane with charge. The protein of interest and the fusion partner applicable to the present invention can be peptide or protein which has isoelectric point difference of 1 or more, preferably 1.5 or more, more preferably 2 or more. For examples, the protein of interest can be a protein having isoelectric point of 7.0 or more, or 7.0 or less.

In one aspect, the present invention provides an efficient process for separating or purifying the protein of interest comprising:

a) expressing a fusion protein comprising a protein of interest, and a fusion partner in host cell, wherein the fusion partner includes an amino acid sequence having a different charge from that of the protein of interest at N-terminal or internal site, and an amino acid sequence to be cleaved with the ubiquitin cleavage enzyme at C-terminus;

b) loading cell extract containing the fusion protein on matrix where the fusion protein can adsorb;

c) treating the adsorbed matrix with the ubiquitin cleavage enzyme; and d) eluting the cleaved protein of interest from the matrix.

In another aspect, the present invention provides an efficient process for separating or purifying the protein of interest comprising:

a) expressing a fusion protein comprising a protein of interest and a fusion partner in a host cell, wherein the fusion partner includes an amino acid sequence having a different charge from that of the protein of interest at N-terminal or internal site, and an amino acid sequence to be cleaved with the ubiquitin cleavage enzyme at C-terminus;

b) loading cell extract containing the fusion protein on matrix which the fusion partner can adsorb;

c) recovering the fusion protein from the matrix;
d) treating the recovered fusion protein with the ubiquitin cleavage enzyme; and
e) separating the protein of interest from the fusion partner by using the adsorption difference on matrix between the protein of interest and the fusion partner.

In an embodiment of the present invention, the present invention provides a process for preparing the protein of interest with pI of 7.0 or less. More specifically, a fusion protein comprising the protein of interest is adsorbed on matrix, and then the fusion protein adsorbed on the ion exchange resin or membrane is directly treated with the ubiquitin cleavage enzyme without eluting the fusion protein, so as to produce the protein with high purity. This process comprises the steps of expressing the fusion protein comprising the protein of interest with pI of 7.0 or less and the fusion partner where the fusion partner includes an amino acid sequence to be cleaved by ubiquitin cleavage enzyme at C-terminus, and an amino acid sequence at least two positively-charged amino acids at N-terminal or internal site, loading the cell extract containing the fusion protein on ion exchange resin or membrane which the fusion partner can adsorb, treating the ion exchange resin with the ubiquitin cleavage enzyme, and eluting the protein of interest from the ion exchange resin or membrane.

Before treating with the ubiquitin cleavage enzyme, the contaminant proteins, endotoxin and nucleic acid derived from host cell which weakly adsorb the matrix can be dissociated by washing resin tower with salt solution of such a low concentration that the fusion protein cannot dissociate, thereby increasing the purity of the final product. After the enzymatic cleavage of the fusion protein, the protein of interest can be selectively eluted in high purity by applying a salt solution of such a low concentration that only the protein of interest can be eluted.

In another aspect, the present invention provides a process of preparing the protein of interest with pI of 7.0 or less. More specifically, The process comprises the steps of expressing the fusion protein comprising the protein of interest with pI of 7.0 or less and the fusion partner, where the fusion partner includes an amino acid sequence to be cleaved by ubiquitin cleavage enzyme at C-terminus and an amino acid sequence at least two positively-charged amino acids at N-terminal or internal site, loading the cell extract containing the fusion protein on cation exchange resin which the fusion partner can adsorb, recovering the fusion protein from the cation exchange resin or membrane, treating the recovered fusion protein with the ubiquitin cleavage enzyme, and separating the protein of interest by using the adsorption difference on ion exchange resin between the fusion partner and the protein of interest. For example, the step of separating the protein of interest from the fusion partner by using the adsorption difference on matrix can be performed by loading the fusion protein treated with the ubiquitin cleavage enzyme on anion exchange resin to elute the fusion partner, and then eluting the adsorbed protein of interest after adsorbing the fusion protein, or by loading the fusion protein treated with ubiquitin cleavage enzyme on cation exchange resin to adsorb the fusion partner, and then eluting the protein of interest.

In the embodiment of the present invention, the present invention provides a process for preparing the protein of interest with pI of 7.0 or more. More specifically, the process comprises the steps of expressing the fusion protein comprising the protein of interest with pI of 7.0 or more and the fusion partner where the fusion partner includes an amino acid sequence to be cleaved by ubiquitin cleavage enzyme at C-terminus and an amino acid sequence at least two negatively-charged amino acids at N-terminal or internal site, loading the cell extract containing the fusion protein on cation exchange resin which the protein of interest can adsorb, recovering the fusion protein from the cation exchange resin, loading the fusion protein on anion exchange resin which the fusion partner can adsorb, recovering the fusion protein from the anion exchange resin, treating the recovered fusion protein with the ubiquitin cleavage enzyme, and separating the protein of interest by using the adsorption difference on anion exchange resin.

In particular, because most of intracellular proteins have isoelectric point close to weak acid pH, the proteins, nucleic acids, and endotoxin in cell extracts are negatively charged at pH 7.0. According to the present invention, the fusion partner can be modified to include an positively-charged amino acid sequence. Thus, Most of intracellular proteins, nucleic acids, and/or endotoxin can easily be eliminated by passing the cell extract containing the fusion protein through cation exchange resin.

The cation exchange resins applicable to the present invention include CM Sepharose, SP Sepharose, etc. The anion exchange resins include Q Sepharose, DEAE Sepharose, etc.

In the present invention, cell extract of host obtained after the production of the fusion protein can be made to directly enter the expanded bed absorption step, so as to reduce the number of early separation steps such as centrifugation and filtration, and to perform the adsorption and cleavage in a step. The expanded bed adsorption chromatography can remove solid contaminants from cell extract, and provide the desired protein in a step, so that the chromatography can replace initial separation process such as centrifugation and filtration of existing production method.

The purity of the protein of interest can be measured with reverse-phase HPLC. According to the process of the present invention, the amounts of DNA and endotoxin mixed in the protein of interest can decrease.

In the present invention, various proteins can be fused to the fusion partner and expressed in the suitable prokaryotic and eukaryotic cell by using a suitable expression system.

The invention is further illustrated by the following Examples. The following examples are intended only to illustrate the invention and are not intended to limit the scope of the invention as recited by the claims.

Example 1

Producing Expression Fector for K6Ub-hGH

A gene encoding human growth hormone (Genbank Accession No. K02382, Human growth hormone synthetic gene, complete CDS) was cloned into pGNX2 vector (Korean Patent Publication No. 0319520) to produce pGNX2hGH. 400-bp of product was amplified by using the pGNX2hGH as a template and hGHN and hGHCB (Table 1) as primers, and then cleaved by BamH1.

A gene encoding ubiquitin was amplified by using a gene of Genbank Accession No. M17524 (Synthetic human ubiquitin gene, complete cds) as a template and a forward primer (5'-GCAGCATATGCAGATTTTCGTC-3' (UBF) (SEQ ID NO:1) and a backward primer (5'-CGACGGCGCCAC-CTCTTAGCC-3'(UBR)) (SEQ ID NO:2) through PCR, and then 230-bp of amplification product was cleaved by NdeI. The resultant product was ligated with pUC 18 which was cleaved with HindIII to produce pUC18Ubq. To fuse hGH gene, the pUC18Ubq was cleaved with sfo1 and BamH1, and then was fused with 400-bp of PCR product to produce pUC18ubhGH. To transfer pUC18ubhGH to the expression vector, pGNX4 (Korean Patent Publication No. 0319520) and pUC18ubhGH were cleaved by Nde1 and BamH1, and then ligated to produce pGNX4ubhGH. *E. coli* XL1-Blue MR was transformed by pGNX4ubhGH, screened in the medium containing Kanamycin, and then cultured in LB liquid medium. At cell density of OD.sub.600=0.6, the expression of human growth hormone in the cell was induced by addition of 0.5 mM IPTG, and the expression was confirmed by SDS-PAGE analysis.

To fuse 6 lysine tag to the N-terminus of fusion protein, a strand of lysine tag, KTT (Table 1) was synthesized and amplified by using 5'-primer(KTN) and 3'-primer(KTC) through PCR to obtain 45-bp of PCR product. The PCR product was cleaved by NdeI (NEB, England) and AseI (NEB, England), and fused with pGNX4U bhGH cleaved with NdeI to produce pGNX4K6UbhGH. *E. coli* XL1-Blue MR was transformed by pGNX4K6UbhGH, screened in the medium containing Kanamycin, and then cultured in LB liquid medium with shaking. The expression of human growth hormone in the cell was induced by addition of 1 mM IPTG, and the expression was confirmed by SDS-PAGE analysis. The sequence analysis of the expressed plasmid DNA confirmed that 6 lysine tag at N-terminus was encoded by the codons of AAG AAA AAA AAG AAA AAG (SEQ ID NO: 22).

Example 2

Producing Expression Vector for K10-UBP

To clone the UBP 1 gene, the genome of *S. cerevisiae* ATCC 208275 was used as a template and amplified by using the primers of UBPN and UBPC (Table 1) through PCR to produce 2400-bp of UBP1 gene. The UBP 1 was cloned between NdeI and BamH1 site of pRSETc vector. The cloned vector and pGNX4 vector were cleaved with NdeI and BamHI and fused to obtain pGNX4UBP1. *E. coli* XL1-Blue MR was transformed by pGNX4UBP1, screened in the medium containing Kanamycin, and then cultured in LB liquid medium containing Kanamycin. At the cell density of $OD_{600}$=0.6, the expression of UBP 1 in the cell was induced by addition of 0.5 mM IPTG. The activity of UBP 1 was determined by cleaving the fusion protein of Example 1 with the UBP 1.

To easily purify with maintaining the UBP 1 activity, the 10 lysine tag was ligated to the N-terminus of the fusion peptide. 10K (Table 1) of the oligonucleotide having 10 AAG codons was synthesized, and the Nde1 and Ase1 sites in the 10K were cleaved by the restriction enzymes, and then fused with pGNX4UBP1 cleaved with Nde1 and CIP to produce pGNX410KUBP1. The activity of UBP 1 was determined with the same method as pGNX4UBP1.

The primer sequences used in Examples 1 and 2 are shown in the following Table 1.

TABLE 1

| Primer | Nucleic acid sequence(5'(3') | SEQ ID NO. |
|---|---|---|
| UBF | 5'-GCAGCATATGCAGATTTTCGTC-3' | 1 |
| UBR | 5'-CGACGGCGCCACCTCTTAGCC-3' | 2 |
| hGHN | 5'-TTTCCAACCATTCCACTG-3' | 3 |
| hGHCB | 5'-GACTGGATCCTTAAAAACCACAAGAACC-3' | 4 |
| KTN | 5'-GGGGAATTCCATATG-3' | 5 |
| KTT | 5'-GGGGAATTCCATATGAARAARAARAARAARAATAATGGATCCCCC-3' | 6 |
| KTC | 5'-GGGGGATCCATTAAT-3' | 7 |
| UBPN | 5'-CTAGGGCGGTTCATATGGCTTTTGTTTATTGAAAGAAG-3' | 8 |
| UBPC | 5'-ATTGGATCCTTAGTTTACATCTTTACC-3' | 9 |
| 10K | 5'-GGCCATATG(AAG)10ATTAATGGCC-3' | 10 |

Note:
R is Adenine or Guanine

Example 3

Producing and Separating the Fusion Protein

*E. coli* TG1 was transformed with the expression vector pGNX4K6UbhGH obtained in Example 1 to produce transformant colony. The transformant colony was inoculated in 5 mL of LB medium containing 50 mg/L of Kanamycin, and cultured at 37° C. 1 mL of cultured transformant was inoculated in 100 mL of R media containing 5 g/L glucose (the composition of R media is shown at Table 1) and cultured at 30° C. The resultant culture was inoculated in 1.4 L of R media containing 15 g/L glucose, and cultured according to fed-batch culture method where the 500 g/L of glucose solution was added at the time of glucose amount of 0 g/L. When the Absorbance of culture solution reached about 70, the expression of protein was induced by addition of 1 mM IPTG. The cell was harvested with centrifugation, suspended in 20 mM of phosphate buffer solution (pH 7.5), and then disrupted with microfluidizer. The cell extract was centrifuged at 15,000 rpm for 60 minutes to produce supernatant of soluble cell extract, and the soluble cell extract was separated with ion exchange resin.

TABLE 2

| ingredient | Added amount |
|---|---|
| $KH_2PO_4$ | 3 g/L |
| $K_2HPO_4$ | 3 g/L |
| $(NH_4)_2SO_4$ | 4 g/L |

TABLE 2-continued

| ingredient | Added amount |
|---|---|
| Trisodium citrate | 2.3 g/L |
| Casamino acid | 2 g/L |
| Glucose | 5 g/L |
| MgSO$_4$7H$_2$O | 0.22 ml/L |
| Trace metal solution | 1 ml/L |
| Kanamycin | 100 mg/L |
| Thiamine | 5 mg/L |

Econo-Pack column (Bio-Rad, USA) was filed with 2 mL of SP-Sepharose Fast Flow cation exchange resin (Pharmacia, Sweden), and operated at 1 mL/min. Phosphate buffer solution (pH 7.5) was used as a mobile phase, and column was equilibrated with 15 bed volumes of phosphate butter before loading sample. The column was loaded with the supernatant solution, washed with 3 bed volumes of buffer solution, and eluted by various solutions containing the same buffer substance of mobile phase and NaCl in various concentration. Namely, 6 ml of buffer solutions with NaCl concentration of 200, 400, 600, 800, and 1000 mM were used respectively, and the column was washed with 6 bed volumes of 1 M NaCl buffer solution after elution. The fractions obtained by using the elution solution with the various salt concentration were analyzed by SDS-PAGE, and the result was shown in FIG. 2. (SM: Molecular weight marker, 1: a flow through fraction, 2: a solution eluted by buffer solution, 3: a solution eluted by a buffer solution with 200 mM NaCl, 4: a solution eluted by a buffer solution with 400 mM NaCl, 5: a solution eluted by a buffer solution with 600 mM NaCl, 6: a solution eluted by a buffer solution with 800 mM NaCl, 7: a solution eluted by a buffer solution with 1M NaCl).

Figure 2:
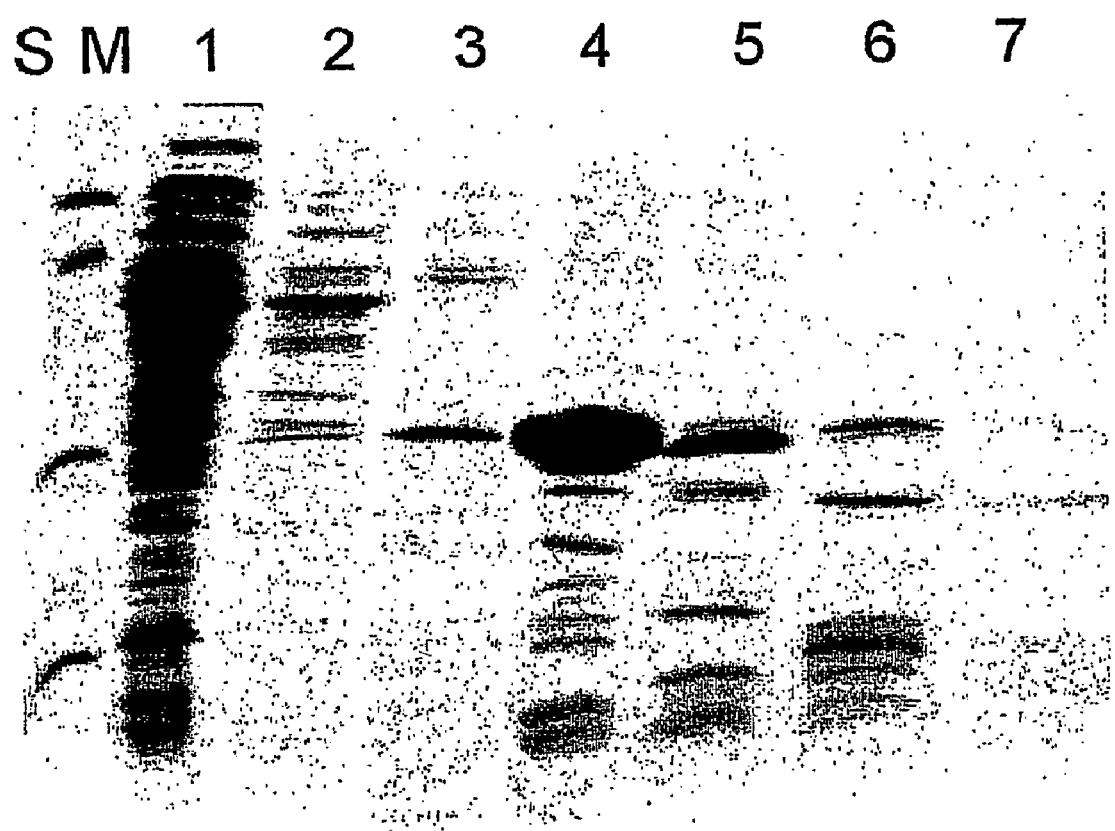
FIG. 2 is a photograph of SDS-PAGE analyzing fractions of the fusion protein eluted on various salt concentration, when the fusion protein is separated by cation exchange chromatography according to Example 3.

As shown in FIG. 2, the fusion protein, K6Ub-hGH was eluted on 400 mM of salt concentration, so as to remove most of contaminant proteins derived from *E. coli*. However, the fusion protein was adsorbed with various cationic proteins.

Example 4

Producing Ubiquitin Cleavage Enzyme

*E. coli* TG1 was transformed with the expression vector, pGNX4K10UBP1 produced in Example 2, and recombinant *E. coli* was cultured according to the method of Example 3 to produce ubiquitin cleavage enzyme fused with 10 lysine tag (K10-UBP). According to substantially the same method of Example 3, the cell extract of recombinant *E. coli* was obtained, and the enzyme was separated by using a cation exchange chromatography. In Example 1, the K6Ub-hGH was eluted by a buffer solution with 400 mM of salt concentration (K6Ub-hGH 400 mM fraction), and in this Example, K10-UBP was also present in a fraction obtained on 400 mM of salt concentration (K10-UBP 400 mM fraction). Accordingly, the solutions containing the two fusion proteins could be adjusted to have the same ionic strength.

Example 5

Figure 3:
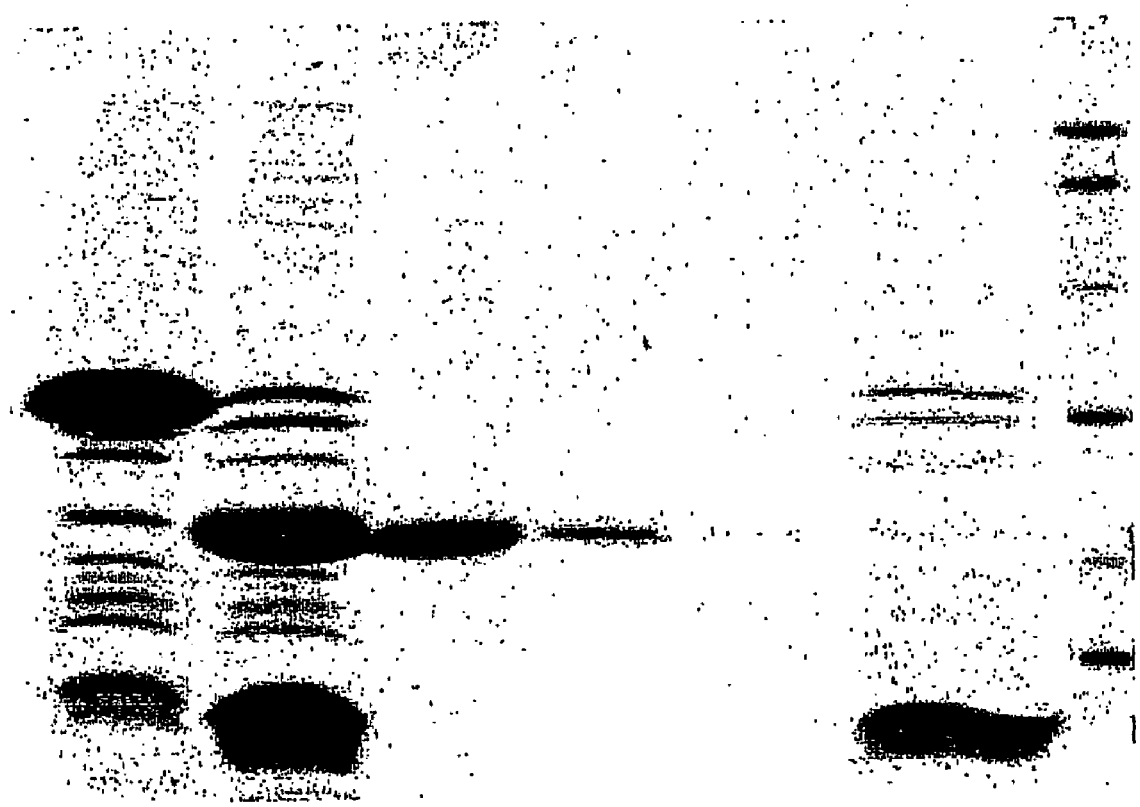
FIG. 3 is a photograph of SDS-PAGE analyzing fractions which are obtained by loading on cation exchange chromatograph, and eluting on 400 mM of salt concentration after treating with ubiquitin cleavage enzyme according to Example 5.

Separating Process by Using Ubiquitin Cleavage Reaction and Cation Exchange Resin The K6Ub-hGH 400 mM fraction partially separated in Example 3, and K10-UBP 400 mM fraction partially separated in Example 4 were mixed in the ratio of 50:1, cleaved at 30° C. for 1 hour, and analyzed by SDS-PAGE (FIG. 3, lane 2).

The reaction solution was diluted with 20 mM phosphate buffer solution (pH 7.5) in the ratio of 1:1 to lower the ionic strength, and loaded on SP-Sepharose Fast Flow cation exchange resin column. The human growth hormone was directly eluted without being adsorbed on the resin. Other proteins were adsorbed on the cation exchange chromatograph, so as to separate the human growth hormone in high yield and purity (FIG. 3, lane 1: K6Ub-hGH 400 mM elution fraction, 2: after treating K6Ub-hGH 400 mM elution fraction with UBP, 3: a flow through solution obtained by eluting the K6Ub-hGH 400 mM solution after treating with UBP, 4: a solution washed by buffer solution, 5: a solution washed by a buffer solution with 200 mM NaCl, 6: a solution washed by a buffer solution with 1M NaCl).

Example 6

Figure 4:
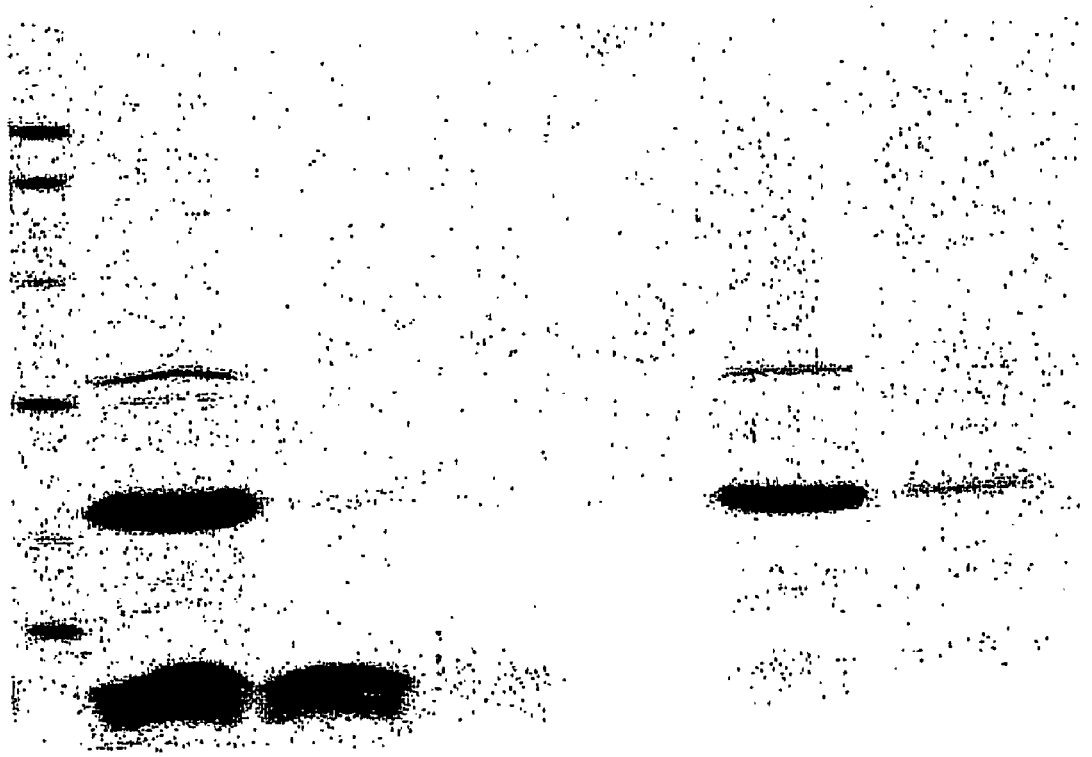
FIG. 4 is a photograph of SDS-PAGE analyzing fractions which are obtained by loading on anion exchange chromatograph, and eluting on 400 mM of salt concentration after treating with ubiquitin cleavage enzyme according to Example 6.

Separating Process by Using the Ubiquitin Cleavage Reaction and Anion Exchange Resin The K6Ub-hGH 400 mM fraction partially separated in Example 3, and The K10-UBP 400 mM fraction partially separated in Example 4 were mixed in the ratio of 50:1, cleaved at 30° C. for 1 hour, and desalted by PD-10 column (Pharmacia) to well adsorb the human growth hormone on anion exchange chromatograph. The desalted reaction solution was loaded on Q-Sepharose Fast Flow anion exchange resin column, and washed with 20 mM phosphate buffer solution to remove unadsorbed proteins. The human growth hormone was eluted by 200 mM salt solution (FIG. 4, lane 1: a solution obtained by treating K6Ub-hGH 400 mM fraction with UBP, 2: a eluted solution obtained by loading the K6Ub-hGH 400 mM after treating with UBP, 4: a solution washed by a buffer solution with 50 mM NaCl, 5: a solution washed by a buffer solution with 200 mM NaCl, 6: a solution washed by a buffer solution with 1M NaCl).

Example 7

Analysis with Reverse-Phase HPLC

Figure 5:
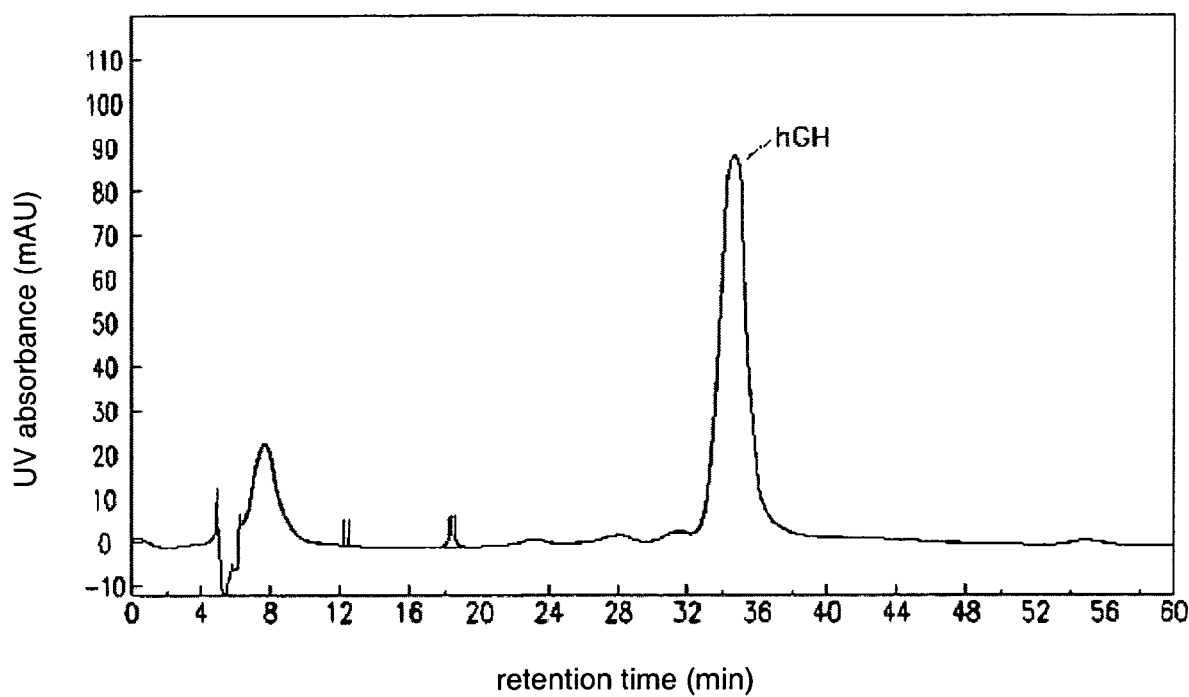
FIG. 5 is a chromatogram analyzing a fraction in lane 3 of FIG. 3 with reverse phase HPLC according to Example 7, wherein the x-axis represents retention time (min) and the y-axis represents UV absorbance (mAU).

To determine the purity of human growth hormone obtained by Example 5, the reverse-phase HPLC was performed. The fraction obtained from the fraction on lane 3 of FIG. 3 was used as a sample. The column was Vydac®C4 (300 A, 5 um, 4.6 mm id×250 mm, USA). The analyzing condition was decided according to the analyzing condition of human growth hormone as described on European Pharmacopeia (European Pharmacopeia 1999: 0951). The temperature of column was maintained at 45° C., and 29% isopropanol and 71% 50 mM Tris buffer solution (pH 7.5) was used as a mobile phase. The flow rate was 250 µl/min. As shown in FIG. 5, the human growth hormone with purity of 99% or more was obtained by using two purification steps of ion exchange resin.

Example 8

Cleavage Reaction in Resin Column

Figure 6:
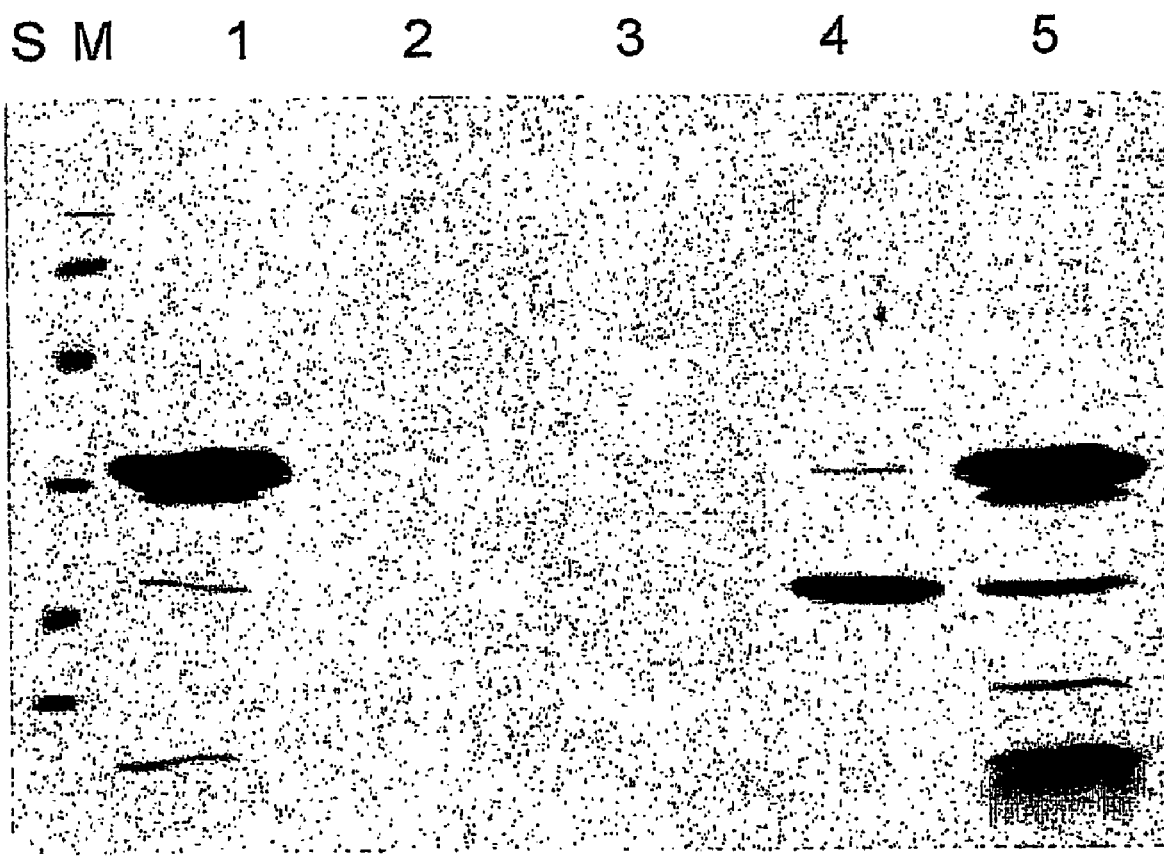
FIG. 6 is a photograph of SDS-PAGE showing that the protein of interest can be prepared in high purity by loading cell lysate including a fusion peptide on cation exchange resin, washing by a salt solution with a low salt concentration, and reacting with ubiquitin cleavage enzyme adsorbed on cation exchange resin.

SP-Sepharose Fast Flow cation exchange column was set according to Example 3, equalized with a phosphate buffer solution (pH 7.5), and then 3 mL of K6UbhGH 400 mM fraction was diluted with the same volume of buffer solution to lower the ionic strength, and injected into the column. The unadsorbed proteins were removed by washing with 6 mL of the buffer solution. 1 mL of a fraction containing K10-UBP 400 mM fraction was diluted with the same volume of buffer solution, injected into the resin tower, and reacted for 1 hour at room temperature. After the reaction, the cleaved human growth hormone was eluted by pouring 6 mL of buffer solution with 200 mM NaCl, and then the remaining adsorbed proteins was eluted by pouring 6 mL of buffer solution with 1M NaCl. The fractions obtained from each step were analyzed by SDS-PAGE to show the result in FIG. 6 (SM: molecular weight marker 1: K6UbhGH 400 mM fraction, 2: a solution washed by buffer solution, 3: a solution eluted after loading K10-UBP 400 mM fraction, 4: a solution washed by a buffer solution with 200 mM NaCl, 5: a solution washed by a buffer solution with 1M NaCl).

The proteins contained in the K6Ub-hGH 400 mM fraction adsorbed well on the cation exchange resin, and thus did not elute during pre-washing step by using the buffer solution (lane 2). Like this, the proteins contained in the K10-UBP 400 mM fraction adsorbed well (lane 3). After the cleavage reaction with ubiquitin cleavage enzyme, the human growth hormone was released from the fusion protein. After cleavage reaction, the tower was poured with a buffer solution with 200 mM NaCl, and then the cleaved human growth hormone was present in the eluted fraction in high purity (lane 4).

Example 9

Applying EBA to Separating Process

Figure 7:
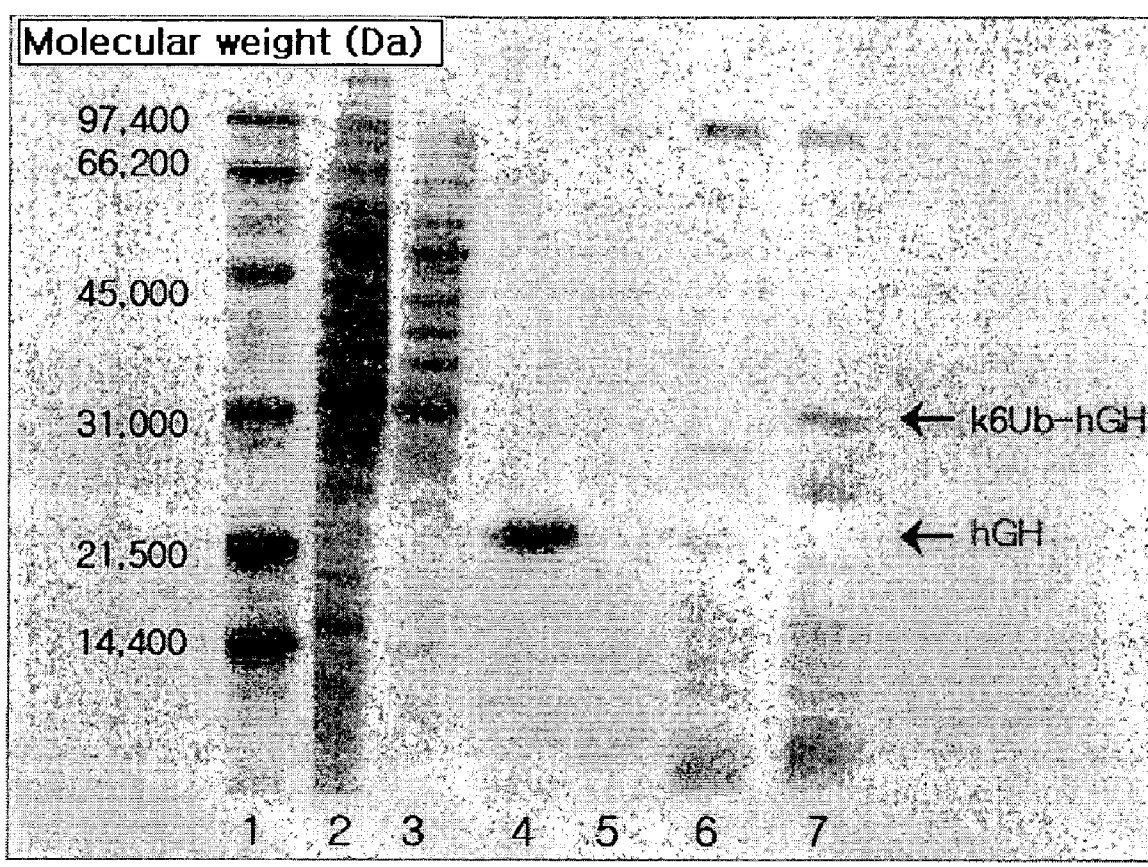
FIG. 7 is a photograph of SDS-PAGE analyzing fractions which are obtained by adsorbing cell extract on cation exchange resin through EBA, precipitating, and reacting with ubiquitin cleavage enzyme in cation exchange resin tower.

STREAMLINE® 25 filled with 100 ml of STREAMLINE® SP resin was equalized with the phosphate buffer solution (pH 7.5), and then injected from down to upward by cell extract (400 ml) containing K6Ub-hGH fusion protein obtained according to Example 3, so that expansion ratio of column bed is 2. After injection of the sample, the column was washed with phosphate buffer solution at 2 times by volume of resin to remove the solid materials such as cell debris, DNA, and cell proteins. To cleave the human growth hormone from fusion protein adsorbed on the resin, the resin was precipitated, and 50 ml of K10-UBP solution obtained in Example 4 was diluted with buffer solution and then was injected into the column. The reaction was performed by circulating the solution in column with peristaltic pump, and the processing degree of cleavage reaction was determined by measuring an absorbance with spectrophotometer. As the reaction processed, the human growth hormone cleaved from the absorbed fusion protein was released increasingly, and after 3 hours, no increase of absorbance confirmed the termination of the reaction. After the reaction, the released human growth hormone was eluted by pouring a buffer solution with 100 mM NaCl, and was washed with solutions containing 600 mM, and 1M NaCl, respectively (FIG. 7, lane 1: molecular weight marker, 2: cell lysate, 3: a solution washed after injecting the cell lysate, 4: a solution eluted after treatment of UBP, 5: a solution washed by a buffer solution with 100 mM NaCl, 6: a solution washed by a buffer solution with 600 mM NaCl, 7: a solution washed by a buffer solution with 1M NaCl).

Example 10

Producing Expression Vector of pGNX4K6UbIFNalpha-2b

To fuse the ubiquitin protein and the interferon protein, two step PCR was performed.

In the first step, the ubiquitin gene was amplified by using the vector including ubiquitin coding gene (Genbank Accession No. M17524, Synthetic human ubiquitin gene, complete cds) as a template and F6KUb (containing Nde I site, 6 lysine, 5'-terminus of ubiquitin as shown in Table 3) and ORIFN (containing 3'-terminus of ubiquitin and 5'-terminus of human interferon) as primers to produce 250-bp and 500-bp of PCR products, respectively.

In the second step, to fuse the two PCR products, the PCR products as templates were amplified with primer F6KUb (containing Nde I site, 6 Lysine, and 5'-terminus of ubiquitin) and primer RIFN (containing 3'-terminus of human interferon; and Bam HI site) to produce 750-bp of PCR product. The resultant product and pGNX4 were cut by NdeI and Bam H1, and ligated to produce pGNX4K6UbIFNalpha-2. The nucleic acid sequence analysis of the vector confirmed that 6 lysine tag, ubiquitin, and human interferon were expressed in a protein.

*E. coli* TG1 was transformed by pGNX4K6UbIFNalpha-2b, and the expression of the fusion peptide was induced by addition of 0.5 mM IPTG, and analyzed with SDS-PAGE. The primer sequences used in the Example were shown in Table 3.

TABLE 3

| Primer | Nucleic acid (5'→3') | Note | SEQ ID NO. |
|---|---|---|---|
| F6Kub | 5'-GGGTTAACATATGGAGGAT GAGGATGAAGACAAGATTTTCG TCAAGAC-3' | Nde I site, ATG, and 6 lysine tag | 11 |
| ORIFN | 5'-AGGGAGATCACAGCCACCT CTTAGCCTTAGCACA-3' | — | 12 |
| OIFN | 5'-TAAGAGGTGGCTGTGATCT CCCTGAGACCCACA-3' | — | 13 |
| RIFN | 5'-GCGCGGATCCTTATTCCTT CCTCCTTAATCTT-3' | TAG and Bam HI site | 14 |

Example 11

Separating Interferon with Cationic Membrane

The *E. coli* TG1 was transformed with pGNX4K6UbIFNalpha-2b, and the clone expressing the fusion protein was selected. The clone was cultured in 5 ml of LB medium and inoculated in 100 ml of LB medium. At the absorbance of 1.5-2, the expression of interferon was induced by addition of IPTG, and the cell was harvested at 4 hours after adding IPTG. The cell was recovered by centrifuging at 1300 rpm for 3 minutes, suspended in 4 ml of 20 mM phosphate buffer solution, and then disrupted by ultrasonicator. The supernatant was obtained by centrifuging cell lysate at 1300 rpm for 30 minutes for use in following separation process.

Figure 8:
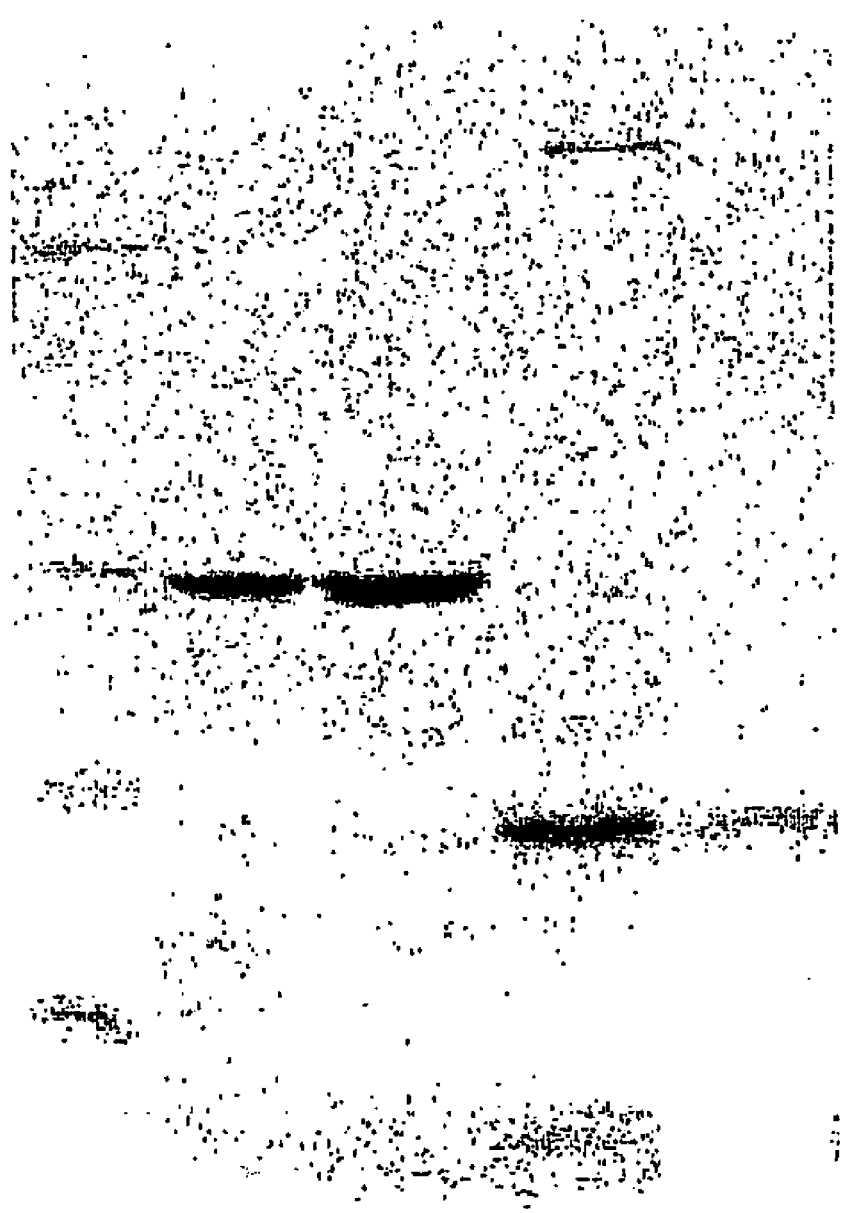
FIG. 8 is a photograph of SDS-PAGE analyzing a sample loaded on membrane, a solution eluted by NaCl solution, a UBP cleavage reaction solution after desalting, and fractions obtained by passing the UBP reaction solution through membrane according to Example 11.

Vivapure S mini H (Vivascience, Germany) cation exchange membrane was used after being equalized with 20 mM phosphate buffer solution for purifying the interferon. The supernatant solution containing interferon was loaded on the membrane, and adsorbed by centrifuging at 1,200 g. The membrane was washed twice with 0.4 ml of phosphate buffer solution, and eluted by phosphate buffer solution with 1M NaCl. 0.1 ml of the eluted fractions was desalted with Dialysis apparatus (Slide-A-Lyzer mini, Pierce, USA) having cut-off of 3500 for 1 hour, and treated with UBP1. After cleavage reaction for 2 hours, the reaction solution was loaded on the membrane equalized with 20 mM phosphate buffer solution, and centrifuged at 1200 g for 5 minutes. The interferon was present in the fraction passing the membrane without adsorbing in high purity (FIG. 8, lane 1: Loading sample diluted in the ration of 1/10, 2: a solution eluted by a buffer solution with 1M NaCl, 3: a UBP cleavage reaction solution after desalting, 4: a fraction passing the membrane after the cleavage reaction).

Example 12

Modifying Ubiquitin

To change the surface charge of the ubiquitin with maintaining the tertiary structure to enable ubiquitin cleavage enzyme to recognize ubiquitin-fusion protein, anionic glutamates on 16 position, 18 position, and 64 position were substituted with arginine or lysine to change the isoelectric point, in consideration of the tertiary structure of ubiquitin. To modify the ubiquitin, two step-PCR were performed.

In the first step of PCR, the primers having different DNA sequence at the target site were used. Namely, primer FMUB1 was used for modifying the glutamate on 16 position, and 18 position of ubiquitin, primer RMUB1 was used for modifying glutamate on 64 position of ubiquitin. The PCR product was amplified by using forward primer of FMUB2 (containing ATG and Nde I site) and backward primer of RMUB2 (containing Sfo I site) to produce the modified ubiquitin gene. The modified ubiquitin gene was cloned into pGEM-T easy vector to produce pGEM-Mub vector. The sequence analysis of the vector confirmed that the desired modified ubiquitin was obtained.

The second step of PCR was performed to fuse the modified ubiquitin gene and human growth hormone gene. The modified ubiquitin was amplified by using the pGEM-Mub as a template, and primer FMUB2 (containing Nde I site, ATG, and 5'-terminus of the modified ubiquitin) and primer ORhGH (containing 3'-terminus of the modified ubiquitin and 5'-terminus of human growth hormone) to produce 250-bp of PCR product.

The human growth hormone gene was amplified by using a vector including a gene encoding human growth hormone (Genbank Accession no. K02382, Human growth hormone synthetic gene, complete cds) as a template, and primer OFhGH (containing 3'-terminus of the modified ubiquitin, and 5'terminus of human growth hormone) and primer RhGH (containing 3'-terminus of human growth hormone and Bam HI site) to produce 600-bp of PCR product. To fuse the PCR products, the PCR products as a template was amplified with primers of FMUB2 (containing Nde I site and 5'-terminus of modified ubiquitin) and RhGH (containing 3'-terminus of human growth hormone, and Bam HI site) to produce 900-bp of PCR product. The fused PCR product and the expression vector of pGNX4 were cleaved by Nde I and Bam HI, and ligated to produce pGNX4MUbhGH vector. The nucleic acid sequence analysis of the vector confirmed that the modified ubiquitin was fused with the human growth hormone.

Example 13

Separating Human Growth Hormone by Using the Modified Ubiquitin

*E. coli* was transformed with pGNX4MUbhGH vector, and the clone expressing the fusion protein was selected. The clone was pre-cultured in 5 ml of LB medium and 3% of culture solution was inoculated in 100 ml of LB medium. When the absorbance was 1.5-2, the expression of the fusion protein was induced by adding IPTG, and the cells were harvested at 4 hours after addition of IPTG. The cell was recovered by centrifuging at 13,000 rpm for 3 minutes, suspended in 20 mM MES buffer to be 50 of absorbance, and disrupted with ultrasonicator. The supernatant solution was obtained by centrifuging cell lysate at 13,000 rpm for 30 minutes, and then used for following separating steps.

Vivapure S mini H (Vivascience, Germany) cation exchange membrane was used after being equalized with 20 mM MES buffer solution for purifying the fusion protein. The supernatant solution containing the fusion protein was loaded on the membrane, and adsorbed by centrifuging at 900 g. The membrane was washed twice with 0.4 ml of MES buffer solution, and eluted by MES buffer solution with 1M NaCl. 0.1 ml of the eluted fractions was desalted with Dialysis apparatus (Slide-A-Lyzer mini, Pierce, USA) having molecular cut-off of 3500 for 1 hour, and treated with UBP1. After cleavage reaction for 2 hours, the reaction solution was loaded on the membrane equalized with 20 mM MES buffer solution, and centrifuged at 900 g for 5 minutes to produce the purified human growth hormone.

Figure 9:
FIG. 9 is a photograph of SDS-PAGE analyzing a sample loaded on membrane, a solution eluted by NaCl solution, a UBP cleavage reaction solution after desalting, and fractions obtained by passing the UBP reaction solution through membrane according to Example 13.

Like the ionic tag fused to N-terminus of ubiquitin, the isoelectric point increased by replacing amino acids in the internal site of ubiquitin, thereby making the modified ubiquitin adsorb on cationic exchange resin and be recognized by ubiquitin cleavage enzyme (FIG. 9, lane 1: Loading sample diluted in the ratio of 1/10, 2: a solution eluted by a buffer solution with 1M NaCl, 3: a fraction obtained by eluting UBP cleavage reaction after desalting, 4: a fraction obtained by passing membrane after the UBP cleavage reaction). The primers were shown in Table 4, where the underlined parts of nucleic acid sequence represented the modified parts.

TABLE 4

| Primer | Nucleic acid sequence | Note | SEQ ID NO |
|---|---|---|---|
| FMUB1 | 5'-CTT TGA CCG GTA AAA CCA TAA CAT TG<u>CGC</u>G TT<u>A</u> AAT CTT CCC ATA CC-3' | Amino acids modified at Glu16, Arg16, Glu18, and Lys18 | 15 |
| FMUB2 | 5'-GGC CGC AT<u>A</u> <u>TGC</u> AGA TTT TCG TCA AGA CTT TGA CCG GTA AAA CC-3' | Nde I site, and ATG | 16 |
| RMUB1 | 5'-CTC TTA GCC TTA GCA CAA GAT GTA AGG TGG A<u>GCG</u>CT TCT GAA TGT TG-3' | Amino acid modified at Glu64, and Arg64 | 17 |

TABLE 4-continued

| Primer | Nucleic acid sequence | Note | SEQ ID NO |
|---|---|---|---|
| RMUB2 | 5'-CGC GGA TCC AGT GGA ATG GTT GGG GCG CCA CCT CTT AGC CTT AGC AC-3' | Sfo I site | 18 |
| OrhGH | 5'-CAG TGG AAT GGT TGG AAA GCC ACC TCT TAG CCT TAG-3' | | 19 |
| OfhGH | 5'-CTA AGG CTA AGA GGT GGC TTT CCA ACC ATT CCA CTG-3' | | 20 |
| RhGH | 5'-GCC GGA TCC TTA AAA ACC ACA AGA ACC-3' | Bam HI site | 21 |

The protein of interest could be separated easily and economically according to the present invention.

---

What is claimed is:

1. A process of separating a protein of interest from a fusion protein, comprising the steps of:
    a) expressing a fusion protein comprising the protein of interest and a fusion partner in a bacterial host cell, wherein the fusion partner is a functional ubiquitin, and the charge of the fusion partner is changed by attaching an amino acid sequence consists of 2-30 amino acids consisting of at least one amino acid selected from the group consisting of histidine, lysine, arginine, glutamic acid, and aspartic acid to N-terminus of the fusion partner, and wherein the amino acid sequence has a different charge from that of the protein of interest to make a difference in the isoelectric point (pI) between the fusion partner and the protein of interest to be at least 1, wherein the protein of interest has pI of 7 or less, and the charge of the fusion partner is changed by attaching an amino acid sequence consists of 2-30 amino acids consisting of at least one amino acid selected from the group consisting of histidine, lysine, and arginine to N-terminus of the fusion partner, or the protein of interest has pI of more than 7, the charge of the fusion partner is changed by attaching an amino acid sequence consists of 2-30 amino acids consisting of at least one amino acid selected from the group consisting of glutamic acid, and aspartic acid to N-terminus of the fusion partner;
    b) loading the fusion protein on a matrix selected from the group consisting of an ion exchange resin and a membrane, wherein the matrix has a charge which is capable of adsorbing the fusion partner;
    c) treating the matrix adsorbing the fusion partner with ubiquitin cleavage enzyme to cleave the protein of interest; and
    d) eluting the cleaved protein of interest from the matrix.

2. The process according to claim 1, wherein the protein of interest is selected from the group consisting of human growth hormone, interferon, interleukin, granulocyte colony stimulating factor, erythropoietin, and insulin.

3. A process of separating a protein of interest from a fusion protein, comprising the steps of:
    a) expressing a fusion protein comprising the protein of interest and a fusion partner in a bacterial host cell, wherein the fusion partner is a functional ubiquitin, and the charge of the fusion partner is changed by attaching an amino acid sequence consists of 2-30 amino acids consisting of at least one amino acid selected from the group consisting of histidine, lysine, arginine, glutamic acid, and aspartic acid to N-terminus of the fusion partner, and wherein the amino acid sequence has a different charge from that of the protein of interest to the fusion partner to make a difference in the isoelectric point (pI) between the fusion partner and the protein of interest to be at least 1, wherein the protein of interest has pI of 7 or less, and the charge of the fusion partner is changed by attaching an amino acid sequence consists of 2-30 amino acids consisting of at least one amino acid selected from the group consisting of histidine, lysine, and arginine to N-terminus of the fusion partner, or the protein of interest has pI of more than 7, the charge of the fusion partner is changed by attaching an amino acid sequence consists of 2-30 amino acids consisting of at least one amino acid selected from the group consisting of glutamic acid, and aspartic acid to N-terminus of the fusion partner;

b) loading the fusion protein onto a matrix selected from the group consisting of an ion exchange resin and a membrane, wherein the matrix has a charge which is capable of adsorbing the fusion partner;

c) recovering the fusion protein from the matrix by eluting;

d) treating the recovered fusion protein with ubiquitin cleavage enzyme; and e) re-loading the ubiquitin cleavage enzyme treated fusion protein onto a matrix selected from the group consisting of an ion exchange resin and a membrane, wherein the matrix has an adsorption difference to the fusion partner and the protein of interest, and separating the protein of interest from the fusion partner by using the adsorption difference on the matrix.

4. The process according to claim 3, wherein the protein of interest is selected from the group consisting of human growth hormone, interferon, interleukin, granulocyte colony stimulating factor, erythropoietin, and insulin.

* * * * *

SEQUENCE LISTING

<160> NUMBER OF SEQ ID NOS: 21

<210> SEQ ID NO 1
<211> LENGTH: 22
<212> TYPE: DNA
<213> ORGANISM: Artificial Sequence
<220> FEATURE:
<223> OTHER INFORMATION: Nucleic acid sequence of UBF

<400> SEQUENCE: 1
gcagcatatg cagattttcg tc                          22

<210> SEQ ID NO 2
<211> LENGTH: 21
<212> TYPE: DNA
<213> ORGANISM: Artificial Sequence
<220> FEATURE:
<223> OTHER INFORMATION: Nucleic acid sequence of UBR

<400> SEQUENCE: 2
cgacggcgcc acctcttagc c                           21

<210> SEQ ID NO 3
<211> LENGTH: 18
<212> TYPE: DNA
<213> ORGANISM: Artificial Sequence
<220> FEATURE:
<223> OTHER INFORMATION: Nucleic acid sequence of hGHN

<400> SEQUENCE: 3
tttccaacca ttccactg                               18

<210> SEQ ID NO 4
<211> LENGTH: 28
<212> TYPE: DNA
<213> ORGANISM: Artificial Sequence
<220> FEATURE:
<223> OTHER INFORMATION: Nucleic acid sequence of hGHCB

<400> SEQUENCE: 4
gactggatcc ttaaaaacca caagaacc                    28

<210> SEQ ID NO 5
<211> LENGTH: 15
<212> TYPE: DNA
<213> ORGANISM: Artificial Sequence
<220> FEATURE:
<223> OTHER INFORMATION: Nucleic acid sequence of KTN

<400> SEQUENCE: 5
ggggaattcc atatg                                                    15

<210> SEQ ID NO 6
<211> LENGTH: 45
<212> TYPE: DNA
<213> ORGANISM: Artificial Sequence
<220> FEATURE:
<223> OTHER INFORMATION: Nucleic acid sequence of KTT

<400> SEQUENCE: 6
ggggaattcc atatgaaraa raaraaraar aataatggat ccccc                   45

<210> SEQ ID NO 7
<211> LENGTH: 15
<212> TYPE: DNA
<213> ORGANISM: Artificial Sequence
<220> FEATURE:
<223> OTHER INFORMATION: Nucleic acid sequence of KTC

<400> SEQUENCE: 7
gggggatcca ttaat                                                    15

<210> SEQ ID NO 8
<211> LENGTH: 38
<212> TYPE: DNA
<213> ORGANISM: Artificial Sequence
<220> FEATURE:
<223> OTHER INFORMATION: Nucleic acid sequence of UBPN

<400> SEQUENCE: 8
ctaccgcggt tcatatggct tttgtttatt gaaagaag                           38

<210> SEQ ID NO 9
<211> LENGTH: 27
<212> TYPE: DNA
<213> ORGANISM: Artificial Sequence
<220> FEATURE:
<223> OTHER INFORMATION: Nucleic acid sequence of UBPC

<400> SEQUENCE: 9
attggatcct tagtttacat ctttacc                                       27

<210> SEQ ID NO 10
<211> LENGTH: 49
<212> TYPE: DNA
<213> ORGANISM: Artificial Sequence
<220> FEATURE:
<223> OTHER INFORMATION: Nucleic acid sequence of 10K

<400> SEQUENCE: 10
ggccatatga agaagaagaa gaagaagaag aagaagaaga ttaatggcc               49

<210> SEQ ID NO 11
<211> LENGTH: 48
<212> TYPE: DNA
<213> ORGANISM: Artificial Sequence
<220> FEATURE:
<223> OTHER INFORMATION: Nucleic acid sequence of F6Kub

```
<400> SEQUENCE: 11
gggttaacat atggaggatg aggatgaaga caagattttc gtcaagac        48

<210> SEQ ID NO 12
<211> LENGTH: 34
<212> TYPE: DNA
<213> ORGANISM: Artificial Sequence
<220> FEATURE:
<223> OTHER INFORMATION: Nucleic acid sequence of ORIFN

<400> SEQUENCE: 12
agggagatca cagccacctc ttagccttag caca                      34

<210> SEQ ID NO 13
<211> LENGTH: 33
<212> TYPE: DNA
<213> ORGANISM: Artificial Sequence
<220> FEATURE:
<223> OTHER INFORMATION: Nucleic acid sequence of OFIFN

<400> SEQUENCE: 13
taagaggtgg ctgtgatctc cctgagaccc aca                       33

<210> SEQ ID NO 14
<211> LENGTH: 32
<212> TYPE: DNA
<213> ORGANISM: Artificial Sequence
<220> FEATURE:
<223> OTHER INFORMATION: Nucleic acid sequence of RIFN

<400> SEQUENCE: 14
gcgcggatcc ttattccttc ctccttaatc tt                        32

<210> SEQ ID NO 15
<211> LENGTH: 47
<212> TYPE: DNA
<213> ORGANISM: Artificial Sequence
<220> FEATURE:
<223> OTHER INFORMATION: Nucleic acid sequenceof FMUB1

<400> SEQUENCE: 15
ctttgaccgg taaaaccata acattgcgcg ttaaatcttc ccatacc        47

<210> SEQ ID NO 16
<211> LENGTH: 44
<212> TYPE: DNA
<213> ORGANISM: Artificial Sequence
<220> FEATURE:
<223> OTHER INFORMATION: Nucleic acid sequence of FMUB2

<400> SEQUENCE: 16
ggccgcatat gcagattttc gtcaagactt tgaccggtaa aacc          44

<210> SEQ ID NO 17
<211> LENGTH: 47
<212> TYPE: DNA
<213> ORGANISM: Artificial Sequence
<220> FEATURE:
<223> OTHER INFORMATION: Nucleic acid sequence of RMUB1

<400> SEQUENCE: 17
ctcttagcct tagcacaaga tgtaaggtgg agcgcttctg aatgttg        47

<210> SEQ ID NO 18
```

-continued

```
<211> LENGTH: 47
<212> TYPE: DNA
<213> ORGANISM: Artificial Sequence
<220> FEATURE:
<223> OTHER INFORMATION: Nucleic acid sequence of RMUB2

<400> SEQUENCE: 18
cgcggatcca gtggaatggt tgggcgcca cctcttagcc ttagcac        47

<210> SEQ ID NO 19
<211> LENGTH: 36
<212> TYPE: DNA
<213> ORGANISM: Artificial Sequence
<220> FEATURE:
<223> OTHER INFORMATION: Nucleic acid sequence of OrhGH

<400> SEQUENCE: 19
cagtggaatg gttggaaagc cacctcttag ccttag                  36

<210> SEQ ID NO 20
<211> LENGTH: 36
<212> TYPE: DNA
<213> ORGANISM: Artificial Sequence
<220> FEATURE:
<223> OTHER INFORMATION: Nucleic acid sequence of OfhGH

<400> SEQUENCE: 20
ctaaggctaa gaggtggctt tccaaccatt ccactg                  36

<210> SEQ ID NO 21
<211> LENGTH: 27
<212> TYPE: DNA
<213> ORGANISM: Artificial Sequence
<220> FEATURE:
<223> OTHER INFORMATION: Nucleic acid sequence of RhGH

<400> SEQUENCE: 21
gccggatcct taaaaccac aagaacc                             27
```